US011157697B2

(12) United States Patent
Hu et al.

(10) Patent No.: US 11,157,697 B2
(45) Date of Patent: Oct. 26, 2021

(54) METHOD AND APPARATUS FOR EXTRACTING DIAGNOSIS OBJECT FROM MEDICAL DOCUMENT

(71) Applicant: CANON KABUSHIKI KAISHA, Tokyo (JP)

(72) Inventors: Qinan Hu, Beijing (CN); Yaohai Huang, Beijing (CN); Ruishan Guo, Beijing (CN)

(73) Assignee: CANON KABUSHIKI KAISHA, Tokyo (JP)

( * ) Notice: Subject to any disclaimer, the term of this patent is extended or adjusted under 35 U.S.C. 154(b) by 107 days.

(21) Appl. No.: 16/088,320

(22) PCT Filed: Mar. 22, 2017

(86) PCT No.: PCT/JP2017/011333
§ 371 (c)(1),
(2) Date: Sep. 25, 2018

(87) PCT Pub. No.: WO2017/164204
PCT Pub. Date: Sep. 28, 2017

(65) Prior Publication Data
US 2020/0302117 A1    Sep. 24, 2020

(30) Foreign Application Priority Data

Mar. 25, 2016 (CN) .......................... 201610177996.2

(51) Int. Cl.
| | |
|---|---|
| *G06F 40/295* | (2020.01) |
| *G16H 15/00* | (2018.01) |
| *G16H 50/70* | (2018.01) |
| *G16H 30/40* | (2018.01) |
| *G06F 40/30* | (2020.01) |
| *G06K 9/00* | (2006.01) |

(52) U.S. Cl.
CPC ............ *G06F 40/295* (2020.01); *G06F 40/30* (2020.01); *G06K 9/00442* (2013.01);
(Continued)

(58) Field of Classification Search
USPC .............................................. 704/7–10, 257
See application file for complete search history.

(56) References Cited

U.S. PATENT DOCUMENTS

| | | | |
|---|---|---|---|
| 8,312,018 B2 | 11/2012 | Shami | |
| 2011/0077968 A1* | 3/2011 | Kelly | G16H 50/20 705/3 |

(Continued)

FOREIGN PATENT DOCUMENTS

| | | |
|---|---|---|
| CN | 101297324 A | 10/2008 |
| WO | 2015/114485 A1 | 8/2015 |

OTHER PUBLICATIONS

Attardi, G., et al, "Annotation and Extraction of Relations from Italian Medical Records".

(Continued)

*Primary Examiner* — Leonard Saint Cyr
(74) *Attorney, Agent, or Firm* — Canon U.S.A., Inc. IP Division

(57) ABSTRACT

This invention provides a method for extracting a diagnosis object from a medical document comprises: extracting, from an input medical document, body part entities and at least one type of non-body-part entities and the relations between the body part entities and the non-body-part entities; obtaining, for each pair of all possible pairs of the non-body-part entities, a relevance score between two non-body-part entities within one pair, wherein the relevance score is obtained by using the relations between the two non-body-part entities within one pair and one or more body part entities in a plurality of historical medical documents; clustering the non-body-part entities in the input medical document into one or more clusters based on the relevance scores of the all possible pairs; and outputting one or more body part entities (Continued)

related to one or more non-body-part entities clustered in each of the clusters as one diagnosis object.

26 Claims, 9 Drawing Sheets

(52) U.S. Cl.
CPC .............. *G16H 15/00* (2018.01); *G16H 30/40* (2018.01); *G16H 50/70* (2018.01)

(56) References Cited

U.S. PATENT DOCUMENTS

| | | | |
|---|---|---|---|
| 2013/0060793 A1 | 3/2013 | Bandyopadhyay | |
| 2015/0019246 A1* | 1/2015 | Inoue | G16H 15/00 705/2 |
| 2017/0343634 A1* | 11/2017 | Lencz | A61B 5/055 |

OTHER PUBLICATIONS

Ko, B. C., et al, "Automatic medical image annotation and keyword-based image retrieval using relevance feedback", J Digit Imaging, 2012, pp. 454-465, vol. 25.

Ye Feng et al.; "Intelligent Recognition of Named Entity in Electronic Medical Records;" Chinese Journal of Biomedical Engineering; vol. 30, No. 2; Apr. 2011; pp. 1-8.

Yang Jin-Feng et al.; "Corpus Construction for Named Entities and Entity Relations on Chinese Electronic Medical Records;" Journal of Software, vol. 27, No. 11; Mar. 22, 2016, pp. 2725-2746.

Yang Jin-Feng et al.; "An Overview of Research on Electronic Medical Record Oriented Named Entity Recognition and Entity Relation Extraction;" Acta Automatica Sinica; vol. 40, No. 8, 2014-08-31; pp. 1-26.

\* cited by examiner

[Fig. 1]
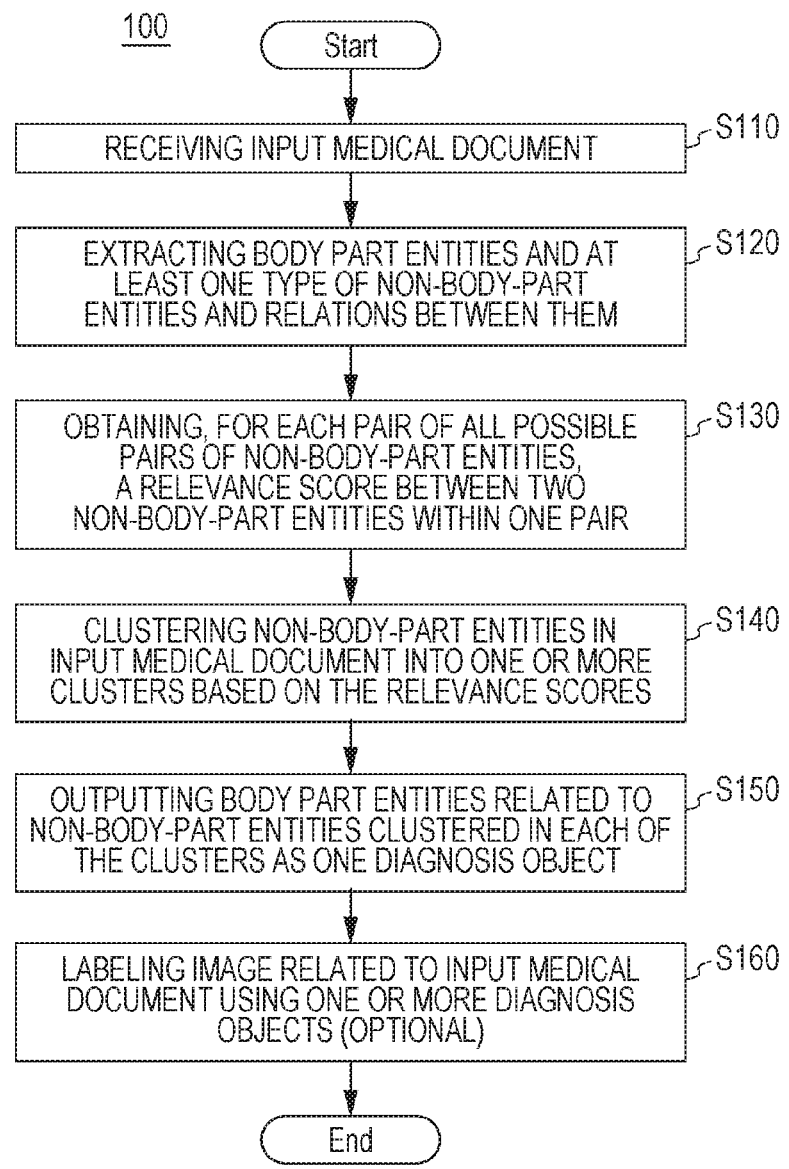

[Fig. 2]

Object of Exam
Examine the lung in detail
<Image Observations>
A nodule of about 3cm in the right lung S5 is observed.
The right hilar and mediastinum lymph node enlargement is observed.
It is observed that a diffuse cavity is formed in the left middle lobe.
An emphysematous variation in the left upper lobe is observed. A bulla with a major diameter of 7cm is seen.
<Impression>
Primary lung cancer is suspected.
It is considered as an observation of honeycomb lung.
It is considered as pulmonary emphysema.

[Fig. 3]
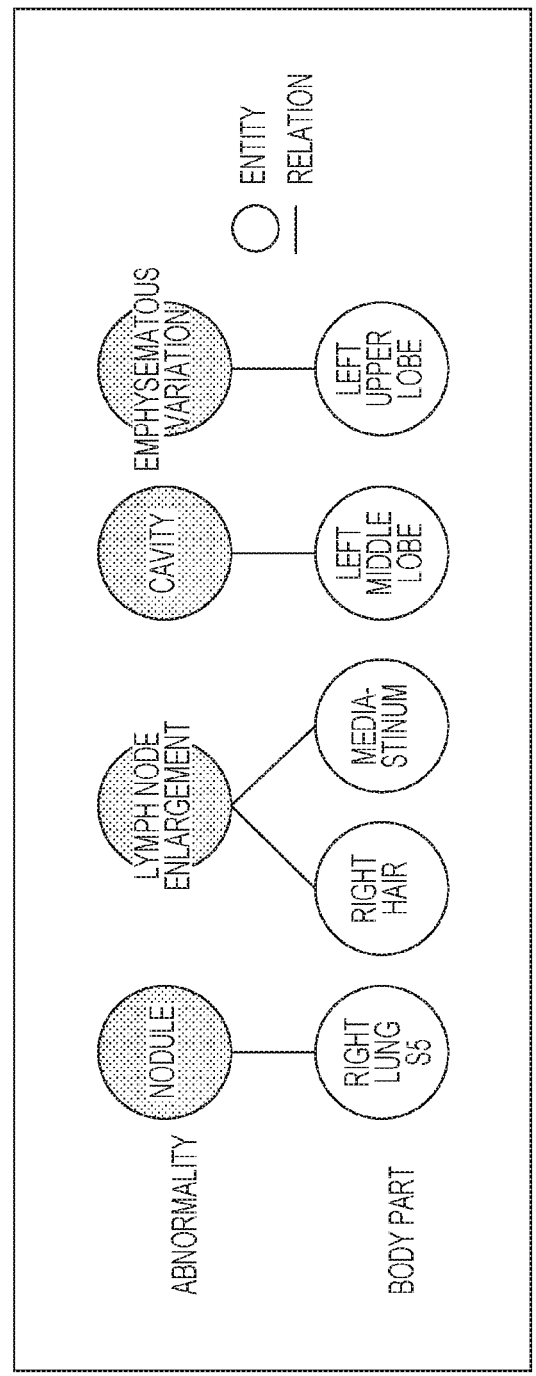

[Fig. 4]
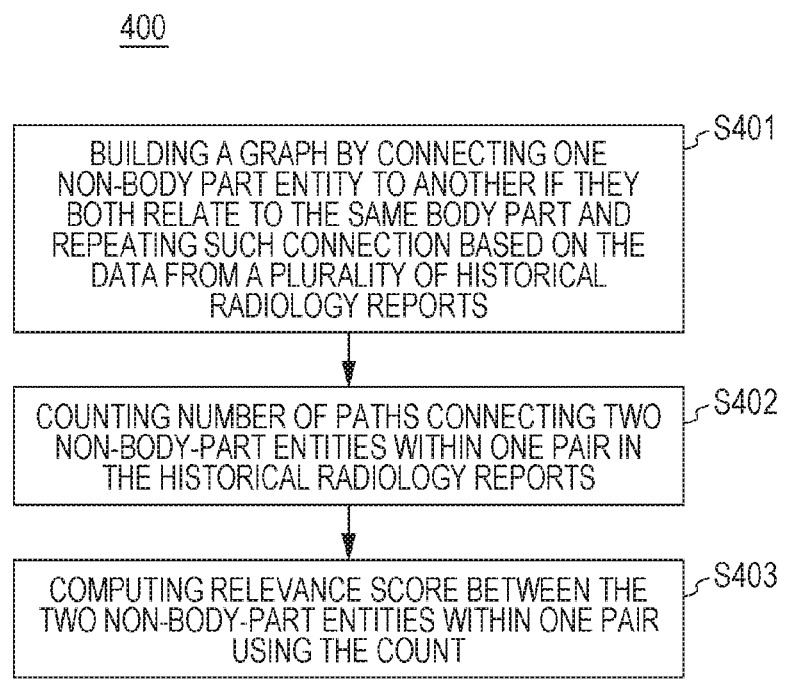

[Fig. 5]
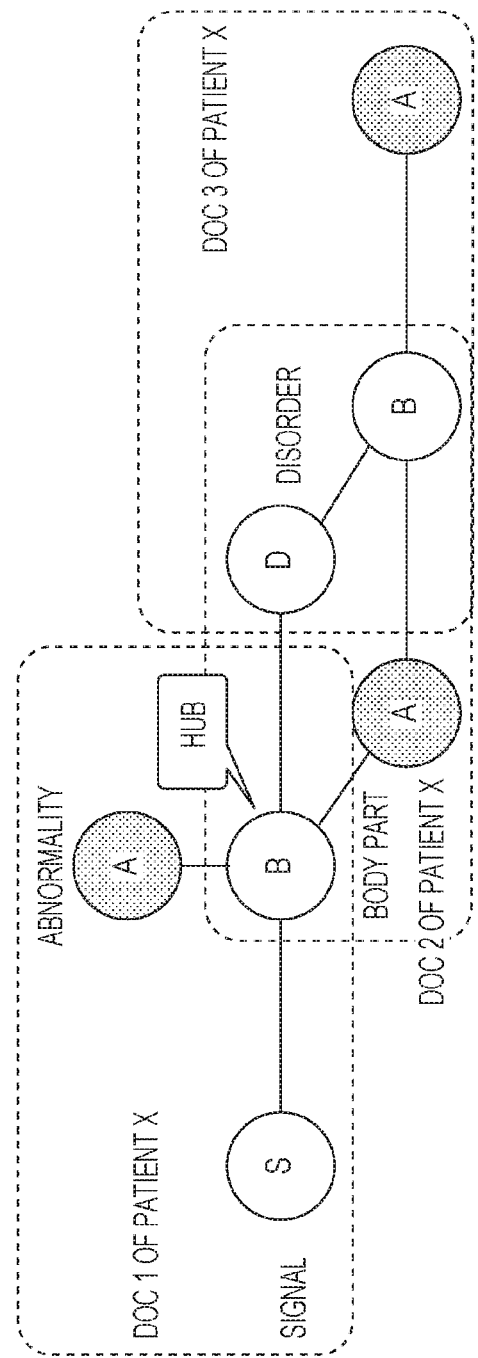

[Fig. 6]

| PATHS | SEMANTIC MEANING | EXAMPLES (NODULE VS. LYMPH NODE ENLARGEMENT) | COUNT |
|---|---|---|---|
| A-(B)-A | AI,AJ ARE FOUND AT THE SAME BODY PART | NODULE - VOCAL CORD FILM - LYMPH NODE ENLARGEMENT | 25 |
| | | NODULE - THYROID - LYMPH NODE ENLARGEMENT | 64 |
| | | NODULE - SINOATRIAL NODE - LYMPH NODE ENLARGEMENT | 37 |
| | | NODULE - APEX OF LUNG - LYMPH NODE ENLARGEMENT | 74 |
| | | NODULE - ABDOMINAL CAVITY - LYMPH NODE ENLARGEMENT | 28 |
| A-(B)-A-(B)-A | AI,AJ CO-OCCUR WITH THE SAME ABNORMALITY | NODULE - SINOATRIAL NODE - HYPERTROPHY - LEFT ATRIUM - LYMPH NODE ENLARGEMENT | 5 |
| A-(B)-D-(B)-A | AI,AJ ARE OF THE SAME DISORDER | NODULE - APEX OF LUNG - LUNG CANCER - PLEURA - LYMPH NODE ENLARGEMENT | 56 |
| | | NODULE - THYROID - THYRONCUS - THYROID - LYMPH NODE ENLARGEMENT | 12 |

| RELEVANCE SCORES | NODULE | LYMPH NODE ENLARGEMENT | CAVITY | EMPHYSEMATOUS VARIATION |
|---|---|---|---|---|
| NODULE | 1 | 0.9 | 0.7 | 0.8 |
| LYMPH NODE ENLARGEMENT | | 1 | 0.2 | 0.9 |
| CAVITY | | | 1 | 0.1 |
| EMPHYSEMATOUS VARIATION | | | | 1 |

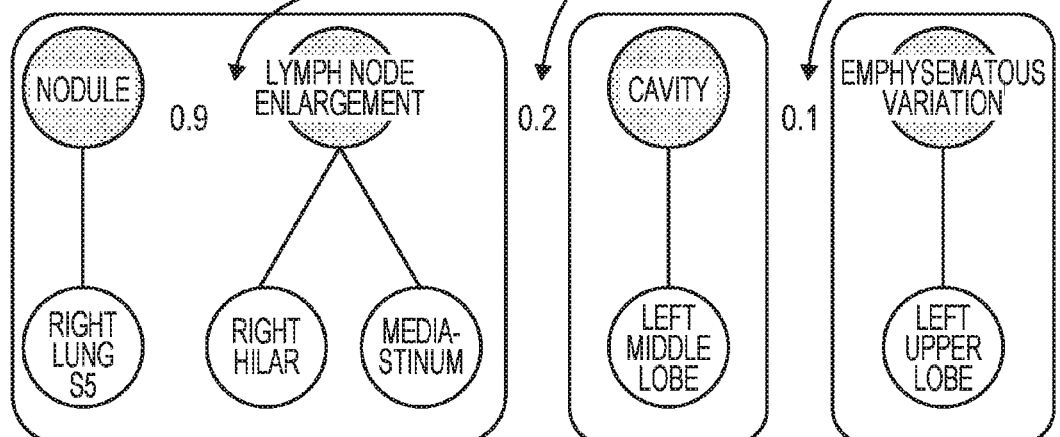

[Fig. 7]

| Diagnoses (Optional) | Diagnoses objects | Body parts | May 3, 2013 |
|---|---|---|---|
| primary lung cancer | right lung S5, right hilar, mediastinum "1" | right lung S5 | a nodule of 3 cm(+) |
| | | right hilar mediastinum | lymph node enlargement(+) |
| honeycomb lung | left middle lobe "2" | left middle lobe | diffuse cavity(+) |
| pulmonary emphysema | left upper lobe "3" | left upper lobe | emphysematous variation(+) a bulla of 7 cm(+) |

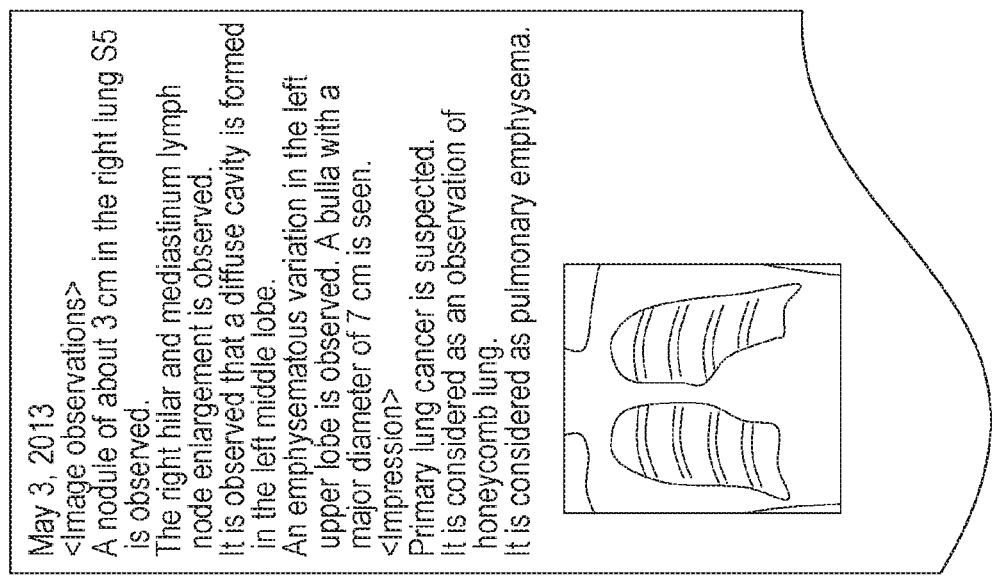

May 3, 2013
<Image observations>
A nodule of about 3 cm in the right lung S5 is observed.
The right hilar and mediastinum lymph node enlargement is observed.
It is observed that a diffuse cavity is formed in the left middle lobe.
An emphysematous variation in the left upper lobe is observed. A bulla with a major diameter of 7 cm is seen.
<Impression>
Primary lung cancer is suspected.
It is considered as an observation of honeycomb lung.
It is considered as pulmonary emphysema.

[Fig. 8]
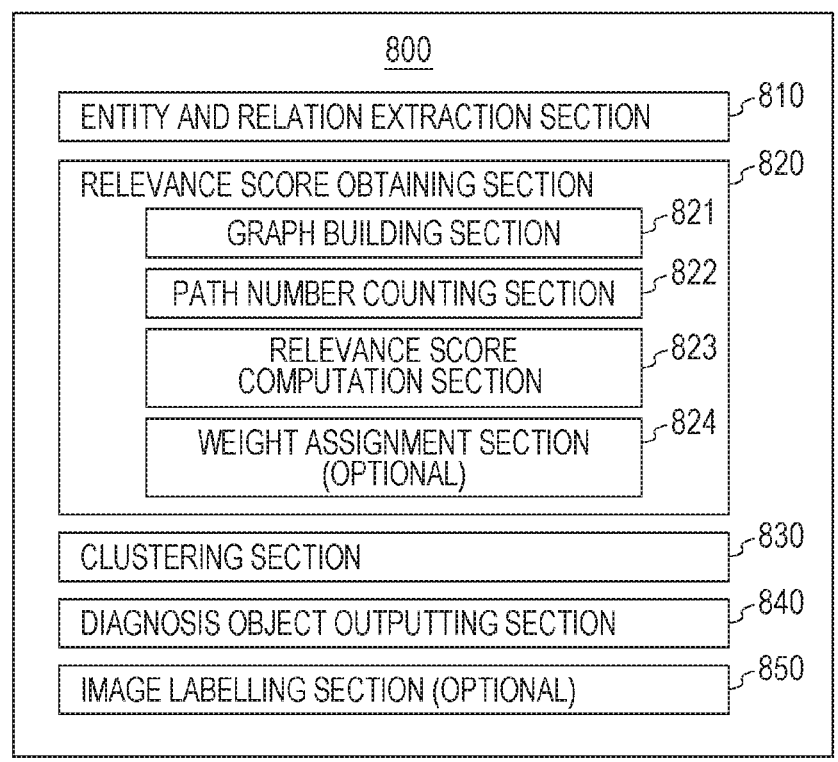

[Fig. 9]
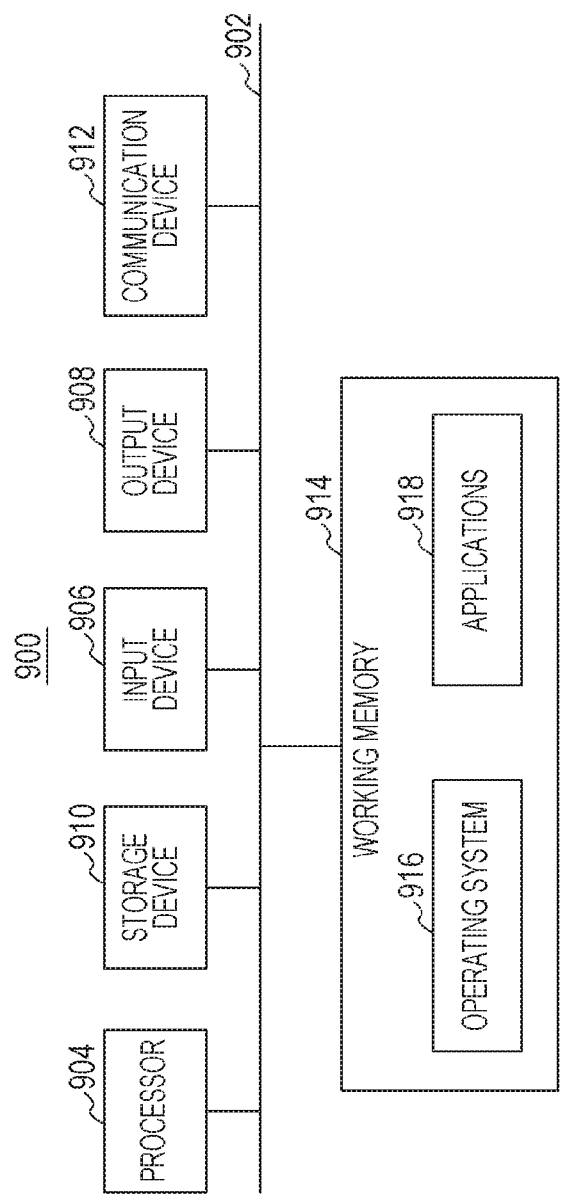

METHOD AND APPARATUS FOR EXTRACTING DIAGNOSIS OBJECT FROM MEDICAL DOCUMENT

CROSS-REFERENCE TO RELATED APPLICATIONS

This application is a National Phase application of International Application No. PCT/JP2017/011333, filed Mar. 22, 2017, which claims the benefit of Chinese Patent Application No. 201610177996.2, filed Mar. 25, 2016. The disclosures of the above-named applications and patent are hereby incorporated by reference herein in their entirety.

TECHNICAL FIELD

The present disclosure relates to a field of text information extraction, and in more particular, relates to a method and apparatus for extracting a diagnosis object from a medical document.

BACKGROUND ART

The technologies for extracting a diagnosis object, i.e., a set of entities, from a medical document are known. The diagnosis object here refers to one or more entities involved when making a specific diagnosis. In other words, the diagnosis object refers to one or more entities which are considered together to make a specific diagnosis. The entity here refers to the wording that represents a specific medical conception, such as a body part, in the medical document. According to the technologies in the prior art, the diagnosis object, i.e., the set of entities, is extracted according to the concepts of the entities. In a case where a set of the body part entities are extracted as one diagnosis object, the same diagnosis objects will be extracted if the same body part entities are comprised in the medical documents. But the fact is that, with respect to different medical documents, even if the same body part entities are comprised therein, the diagnoses made therein may be different. Thus, in the prior arts, the diagnosis objects are extracted from a medical document independent of the diagnoses made therein.

In particular, the following two medical documents, Report 1 and Report 2, shown in Table 1 will be discussed. As can be seen from the Table 1, the two Reports relate to the same body part entities, that is, right lung S5, right hilar, mediastinum, left middle lobe, and left upper lobe. But the different diagnoses are made. The diagnosis objects extracted according to the prior arts are shown in the third row of the Table 1. The body part entity or entities within "{ }" belong to one diagnosis object. The same diagnosis objects are extracted for Report 1 and Report 2, because in the prior arts, the body part entities are grouped according to the concepts or medical concepts of the body parts without considering the made diagnoses.

PTL 1 discloses a method for grouping entities based on standard forms thereof. According to the method disclosed in PTL 1, the same grouping results as shown in the third row of the Table 1 will be obtained.

TABLE 1

| Report 1 | Report 2 |
|---|---|
| <Image observations> | <Image observations> |
| A nodule of about 3 cm in the right lung S5 is observed. | A nodule with a diameter of 3 cm in the right lung S5 is observed. |

TABLE 1-continued

| Report 1 | Report 2 |
|---|---|
| The right hilar and mediastinum lymph node enlargement is observed. | The right hilar and the mucosa of the mediastinum impress a little bit thick. |
| It is observed that a diffuse cavity is formed in the left middle lobe. | A tiny cavity structure in the left middle lobe is observed. |
| An emphysematous variation in the left upper lobe is observed. | A discoid atelectasis variation is appeared in the left middle lobe. |
| A bulla with a major diameter of 7 cm is seen. | <Impression> |
| <Impression> | Lung cancer of right lung S5 is strongly suspected. |
| Primary lung cancer is suspected. | It is considered as an observation that interstitial pneumonia variation is suspected. |
| It is considered as an observation of honeycomb lung. | Discoid atelectasis is appeared. |
| it is considered as pulmonary emphysema. | |
| {right lung S5, right hilar}, {mediastinum}, {left middle lobe, left upper lobe} | {right lung S5, right hilar}, {mediastinum}, {left middle lobe, left upper lobe} |

CITATION LIST

Patent Literature

PTL 1; U.S. Pat. No. 8,312,018 B2

SUMMARY OF INVENTION

The inventors of the invention have found that, one medical phenomenon can be expressed with a characterizing sequence (or a path) of several certain types of entities, and that it can be determined whether one medical phenomenon is completely described by detecting whether the above characterizing sequence exists.

The inventors of the invention have further found that, different diagnoses may be made for the same set of body parts and consequently give rise to different diagnosis objects. Thus, there is a need for grouping the entities in a medical document according to the diagnoses made therein. In other words, there is a need for providing a method and apparatus which can partition the entities in a medical document into diagnosis-dependent groups.

In accordance with an aspect of the present disclosure, a method for extracting a diagnosis object from a medical document is provided, comprising: extracting, from an input medical document, body part entities and at least one type of non-body-part entities and the relations between the body part entities and the non-body-part entities; obtaining, for each pair of all possible pairs of the non-body-part entities, a relevance score between two non-body-part entities within one pair, wherein the relevance score is obtained by using the relations between the two non-body-part entities within one pair and one or more body part entities in a plurality of historical medical documents; clustering the non-body-part entities in the input medical document into one or more clusters based on the relevance scores of the all possible pairs; and outputting one or more body part entities related to one or more non-body-part entities clustered in each of the clusters as one diagnosis object.

Further characteristic features and advantages of the present disclosure will be apparent from the following description with reference to the drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 1 is a flowchart showing a method 100 for extracting a diagnosis object from a medical document according to the first embodiment of the present disclosure.

FIG. 2 illustrates an example of the medical document.

FIG. 3 illustrates an example of the body part entities and non-body-part entities and the relations between them extracted from the radiology report (or radiology diagnosis report) as shown in FIG. 2.

FIG. 4 is a flowchart showing a process 400 for computing, for each pair of all possible pairs of the non-body-part entities, a relevance score between two non-body-part entities within one pair according to the first embodiment of the present disclosure.

FIG. 5 illustrates an example of a graph built by connecting one non-body-part entity to another non-body-part entity if both of them are related to the same body part entity based on the data from a plurality of historical medical documents of the same patient.

FIG. 6 illustrates three examples of computing, for each pair of all possible pairs of the non-body-part entities, the relevance score and clustering the non-body-part entities based on the relevance scores of the all possible pairs according to the first embodiment of the present disclosure.

FIG. 7 illustrates an example of the process of labelling an image related to the input radiology report using one or more diagnosis objects according to the first embodiment of the present disclosure.

FIG. 8 is a block diagram showing an apparatus 800 for extracting a diagnosis object from a medical document according to the first embodiment of the present disclosure.

FIG. 9 illustrates a general hardware environment 900 wherein at least one of the first to third embodiments of the present disclosure is applicable in accordance with an exemplary embodiment of the present disclosure.

DESCRIPTION OF EMBODIMENTS

Embodiments of the present disclosure will be described in detail below with reference to the drawings.

Please note that similar reference numerals and letters refer to similar items in the figures, and thus once an item is defined in one figure, it need not be discussed for following figures.

In the present disclosure, the terms "first", "second" and the like are only used to discriminate between elements or steps, but are not intended to indicate a temporal order, a preference or an importance.

In the present disclosure, the term "entity" refers to the wording that represents a specific medical conception in a medical document. In more particular, the term "entity" refers to body part element or non-body-part element, such as abnormality, disorder, signal, request, exam, treatment, drug, or the like, that appears in the text of a medical document, which may be a character, a word, or a group of related characters/words.

The medical document may be any diagnosis related document that comprises an observation (or finding) part and an impression (or diagnosis) part. The medical document may comprise a radiology report, such as a Computed Tomography (CT) diagnosis report, a nuclear magnetic resonance (NMR) diagnosis report, or the like, and other types of reports such as a clinical report, preoperative and postoperative reports, an admission record, a discharge summary, or the like.

The abnormality means an abnormal appearance of a body part. The disorder means a disease or lesion of a body part. The signal means a certain kind of signal appeared in a medical document, for example, the T1W1 low signal, the T2W2 high signal, or the like. The request means the exam(s) or exam item(s) requested to be conducted, such as the CT exam, the NMR exam, or the like. The exam means the exam(s) or exam item(s) that have been conducted, such as the CT exam, the NMR exam, or the like. The treatment means the therapeutic method given in a medical document, such as surgery, more physical exercises, or the like. The drug means the medicines prescribed by the doctor.

The relation between a body part entity and a non-body-part entity may be a one to one correspondence, a one to many correspondence, or a many to one correspondence. If a relation between a body part entity and a non-body-part entity is extracted, it means that the body part entity is related to the non-body-part entity, in other words, the relation between a body part entity and a non-body-part entity means an association relation between them.

First Embodiment

First, the first embodiment of the invention will be described with reference to FIGS. 1-8.

FIG. 1 is a flowchart showing a method 100 for extracting a diagnosis object from a medical document according to the present embodiment of the present disclosure. The steps of the method 100 presented below are intended to be illustrative. In some embodiments, the method may be accomplished with one or more additional steps not described, and/or without one or more of the steps discussed. Additionally, the order in which the steps of method are illustrated in FIG. 1 and described as below is not intended to be limiting. In some embodiments, the method may be implemented in one or more processing devices (e.g., a digital processor, an analog processor, a digital circuit designed to process information, an analog circuit designed to process information, a state machine, and/or other mechanisms for electronically processing information). The one or more processing devices may include one or more modules executing some or all of the steps of method in response to instructions stored electronically on an electronic storage medium. The one or more processing modules may include one or more devices configured through hardware, firmware, and/or software to be specifically designed for execution of one or more of the steps of the method.

As shown in FIG. 1, in step S110, an input medical document is received. An example of the medical document is shown in FIG. 2. In FIG. 2, a radiology report is shown.

In step S120, body part entities and at least one type of non-body-part entities and the relations between the body part entities and the non-body-part entities are extracted from the input medical document. The body part entities and the non-body-part entities may be extracted by using a named entity reorganization algorithm. The relation between a body part entity and a non-body-part entity may be extracted by using a relation extraction algorithm. Alternatively, the relation between a body part entity and a non-body-part entity may be extracted if the body part entity and the non-body-part entity co-occur within a context, e.g., within one or a few sentences.

The named entity reorganization algorithm and the relation extraction algorithm are the algorithms known to those skilled in the art. In particular, the named entity reorganization algorithm may be an algorithm that is based on rules, an algorithm that is based on machine learning, an algorithm that is based on the templates, or the like. Similarly, the relation extraction algorithm may be an algorithm that is based on rules, an algorithm that is based on machine learning, an algorithm that is based on the templates, or the like.

If a non-body-part entity has no explicit relation with any body part entity, a default related body part entity may be assigned to it using a knowledge-base or zero anaphora resolution algorithm. For example, the knowledge-base may be a known medical knowledge database. If a non-body-part entity necessarily relates to a body part entity, then the body part entity will be assigned to the non-body-part entity by default. One example of this situation is, e.g., "duodenal ulcer". Here, if an abdominal exam is conducted, the disorder "ulcer" will necessarily relates to the body part "duodenum", thus the body part entity "duodenum" will be assigned to the non-body-part entity "ulcer" by default. An example of the use of the zero anaphora resolution algorithm will be described below. The following two sentences (i) and (ii) appear one after another in a radiology report. The former involves the body part entity "right lung S4" explicitly, while the latter, implicitly. Thus, the body part entity "right lung S4" will be assigned as a default related body part to the non-body-part entities in the second sentence.

(i) A nodule with a diameter of 2.5 cm in peripheral of right lung S4 is observed.

(ii) The nodule is irregular, and the inside thereof is relatively strong radiographed.

When the relation between a body part entity and a non-body-part entity is extracted, the polarity of the non-body-part entity may be considered. That is, it may be considered whether the polarity of the non-body-part entity is positive or negative. The polarity represents whether an expression comprising the non-body-part entity is a positive one or a negative one. For example, regarding the first sentence as shown in the observation part of the radiology report of FIG. 2 "a nodule of about 3 cm in the right lung S5 is observed", the polarity of the non-body-part entity, that is, nodule (a kind of abnormality) will be treated as positive, To the contrast, if the sentence is "a nodule in the right lung S5 is not observed", then the polarity of the abnormality "nodule" will be treated as negative. If the polarity is negative, the relation between the "nodule" and the "right lung S5" may not be extracted.

When the relation between a body part entity and a non-body-part entity is extracted, the hypernym of an entity may be identified and may be further used. For example, if the right lung S5 inferior lingular segment appears as a body part entity in the input document, the right lung S5 will be identified as its hypernym and will be used in the subsequent processing.

FIG. 3 illustrates an example of the body part entities and non-body-part entities and the relations between them extracted from the radiology report as shown in FIG. 2. In FIG. 3, the circle represents an entity, and the segment connecting two circles represents the relation between a body part entity and a non-body-part entity.

As can be seen from the lower part of FIG. 3, the following body part entities are extracted from the radiology report: right lung S5, right hilar, mediastinum, left middle lobe, and left upper lobe. And, as can be seen from the upper part of FIG. 3, the following non-body-part entities are extracted from the radiology report: nodule, lymph node enlargement, diffuse cavity, and emphysematous variation.

Note that, in the example of FIG. 3, merely one type of the non-body-part entities, that is, the abnormalities are extracted. It can be understood that the invention is not limited thereto. More than one type of the non-body-part entities may be extracted. For example, at least one of the abnormality, the disorder, the signal, the request, the exam, the treatment, and the drug may be extracted if they are available.

And, as also can be seen from FIG. 3, the relation between "right lung S5" and "nodule" is extracted because they co-occur in the same sentence within the radiology report, that is, "A nodule of about 3 cm in the right lung S5 is observed". The other relations between a body part entity and a non-body-part entity are similarly extracted.

In step S130, for each pair of all possible pairs of the non-body-part entities, a relevance score between two non-body-part entities within one pair is obtained. In particular, the relevance score may be obtained by using the relations between the two non-body-part entities within one pair and one or more body part entities in a plurality of historical medical documents.

The operations of step S130 will be described in details with reference to FIGS. 4-5. FIG. 4 illustrates the sub-steps within the step S130. That is, FIG. 4 is a flowchart showing a process 400 for computing, for each pair of all possible pairs of the non-body-part entities, a relevance score between two non-body-part entities within one pair according to the present embodiment of the present disclosure. Note that, the steps of the process 400 may be performed online and the relevance scores may be computed in a real time manner. Alternatively, the steps of the process 400 may be performed offline in advance and the computed relevance scores may be pre-stored, and the pre-stored relevance scores may be retrieved when necessary. FIG. 5 illustrates an example of a graph built by connecting one non-body-part entity to another non-body-part entity if both of them are related to the same body part entity based on the data from a plurality of historical medical documents of the same patient.

Referring to FIG. 4 now, in Step S401, the body part entities and the non-body-part entities and the relations between them are extracted from a plurality of historical radiology reports, and a graph is built by using the extracted entities and the extracted relations. In particular, the graph is build with a body part entity used as the connecting point for the non-body-part entities. And, it is assumed that each non-body-part entity is related to a body part entity. In more particular, first, if one non-body-part entity and another non-body-part entity relate to the same body part entity, then these two non-body-part entities will be connected via this body part entity. Second, such connection is repeated across the plurality of historical radiology reports until there are no more non-body-part entities needed to be connected. It can be understood that, while the graph is built, the paths connecting two different non-body-part entities are built accordingly.

An example of the build graph is shown in FIG. 5. In the graph of FIG. 5, the nodes represent the body part entities and the non-body-part entities, and the edges connecting the nodes represent the relations between the body part entities and the non-body-part entities. In FIG. 5, a body part entity is used as a "hub" (or core node).

As can be seen from FIG. 5, the paths that connect different non-body-part entities have been built. For example, in FIG. 5, two body part entities are shown. For the left side body part entity, the two kinds of different abnormalities next to it are connected to each other because they both relate to this left side body part entity. In other words, a path connecting these two kinds of different abnormalities via one body part entity may be built. Further, similarly, the two kinds of different abnormalities on the left and right sides of the right side body part entity are also connected to each other because they both relate to this right side body part entity. On a basis of this, the abnormality on the top of the left side body part entity and the abnormality on the right side of the right side body part entity may also be connected because they relate to the same abnormality (the abnormality at the bottom of the left side body part entity) via the two body part entities. In other words, a path connecting these two kinds of different abnormalities via two body parts may be built. Alternatively, the abnormality on the top of the left side body part entity and the abnormality on the right side of the right side body part entity may also be connected via the disorder entity, which connects the left and right side body part entities. The graph built as shown in FIG. 5, in more particular, the paths built therein may be used for computing the relevant score between two non-body-part entities, which will be described in details later.

Note that, in the graph of FIG. 5, the paths are built among the entities from the historical radiology reports of the same patient, i.e., the patient X. But the invention is not limited thereto. The paths may be built among the entities from the historical radiology reports of different patients.

Note that, for example, the number of the plurality of historical radiology reports used for building the graph or the paths may be greater than or equal to 100. And preferable, the number of the plurality of historical radiology reports used for building the graph or the paths may be greater than or equal to 100 and less than or equal to one million. It can be understood that, the greater the number of the used historical reports is, the higher the accuracy of the computed relevance score will be.

In Step S402, a number of paths connecting the two non-body-part entities within one pair in the historical radiology reports is counted. In particular, in FIG. 5, the graph built with use of a plurality of historical radiology reports of the patient X is shown. Similarly, such graph may also be built for another patient. If a large amount of graphs, such as hundreds of or thousands of graphs, built in such a way are considered, the number of paths connecting the two non-body-part entities within one pair may be counted and further be used for computing the relevant score. As mentioned previously, the paths connecting the two non-body-part entities within one pair are built with the basic principle that one non-body-part entity is connected to another if they both relate to the same body part entity.

Optionally, the step S402 may further comprise filtering the paths using a property of non-body-part entity as a constraint, wherein the property of non-body-part entity comprise at least one of polarity, patient ID, patient age, patient sex, time span between exams, and body part ontology. For example, with respect to a path connecting two abnormalities via one body part entity, if the polarity of one or both of the abnormalities is negative, then such path will be invalid and will be filtered out and discarded. For another example, assuming that the nodule is found at the vocal cord film in one report, and the lymph node enlargement is also found at the vocal cord film in another report, if the two reports are from two different patients (or two patient IDs), then the path "nodule—vocal cord film—lymph node enlargement" will be invalid and will be filtered out and discarded. Alternatively, also under this consumption, if the time span between the two reports are more than, for example, 2 years, then the path "nodule—vocal cord film—lymph node enlargement" will be invalid and will be filtered out and discarded. The constraint with respect to the patient age or the patient sex may be similarly applied. The body part ontology is a known medical knowledge database wherein the upper level and/or lower level conceptions of a body part entity are recorded. For still another example, with respect to a path connecting two abnormalities via one body part entity, if the lung is the interested body part, then the path comprising, for example, right lung S5, right hilar, left lung middle lobe, left lung upper lobe, or the like will be filtered out for further use.

In Step S403, the relevance score between the two non-body-part entities within one pair is computed using the count. Various computation methods may be used to compute the relevance score. In one embodiment of the invention, the count of the number of the paths on which the two non-body-part entities within one pair co-occur at its two ends, being noted as C1, and the count of the number of the paths on which merely one of the two non-body-part entities within one pair occurs at either one of its two ends (or in other words, the paths on which the two non-body-part entities do not co-occur at its two ends), being noted as C2, are used for computing the relevance score according to the following equation:

[Math.1]

$$S = \frac{C1}{C1 + C2} \quad (1)$$

wherein S represents the relevance score between the two non-body-part entities within one pair, C1 represents the count of the number of the paths on which the two non-body-part entities within one pair co-occur at its two ends, and C2 represents the count of the number of the paths on which merely one of the two non-body-part entities within one pair occurs at either one of its two ends. The relevance score S may take a value greater than or equal to 0 and smaller than or equal to 1. The count C1 or C2 may take a positive integer value greater than or equal to 0.

As can be seen, the bigger the count of the number of the paths on which the two non-body-part entities within one pair co-occur is, the smaller the count of the number of the paths on which the two non-body-part entities within one pair do not co-occur is, and accordingly the higher the relevance score is. Note that the computation method represented by the above equation (1) is merely an exemplary example, and other computation method may also be used. For example, the algorithms, e.g. random walk, or pair-wise random walk may also be used for computing the relevance scores.

Note that, after the graph or paths being built based on the data from a plurality historical radiology reports, the Steps S402 and S403 will be performed repeatedly for each pair of all possible pairs of the non-body-part entities in the input radiology report.

Now returning back to Step S140 of FIG. 1, in Step S140, the clustering of the non-body-part entities, for example, the four abnormalities shown in FIG. 2, in the input radiology report based on the relevance scores of the all possible pairs is performed. A clustering algorithm comprising at least one of k-means, affinity propagation and spectrum clustering may be used for achieving the clustering. For example, the k-means algorithm may be used for clustering the non-body-part entities in the input radiology report into k clusters based on the relevance scores of the all possible pairs. In such a case, the computed relevance scores of the all possible pairs may be used as the parameter "similarities" in the k-means algorithm, and the variable k may be determined by the number of the disorders appeared in the impression part of the input radiology report. In particular, in FIG. 2, three disorders, i.e., primary lung cancer, honeycomb lung, and pulmonary emphysema, are shown in the impression part. Thus, the variable k may be 3. That is, the four abnormalities extracted from the report of FIG. 2 may be clustered into 3 clusters.

In Step S150, one or more body part entities related to one or more non-body-part entities clustered in each of the clusters are output as one diagnosis object. For example, in a case wherein the nodule and the lymph node enlargement are clustered into one cluster, then the body part entities related thereto, that is, as can be seen from FIG. 3, the right lung S5, the right hilar, and the mediastinum, may be output as one diagnosis object.

Optionally, one diagnosis object, i.e., a set of the body part entities may be further related to one disorder based on the known medical knowledge or with use of a known medical knowledge database. For example, one diagnosis object, that is, the clustered body part entities—the right lung S5, the right hilar, and the mediastinum—may be related to the disorder "primary lung cancer" based on the known medical knowledge. In other words, these body parts are considered together to make the diagnosis with respect to "primary lung cancer".

In Step S160, optionally, an image related to the input radiology report may be labelled using one or more output diagnosis objects. This step will be described in details later with reference to FIG. 7.

Next, three examples of the first embodiment will be described with reference to FIG. 6. FIG. 6 illustrates three examples of computing, for each pair of all possible pairs of the non-body-part entities, the relevance score and clustering the non-body-part entities based on the relevance scores of the all possible pairs according to the present embodiment of the present disclosure.

First Example (Use of the Path A-(B)-A)

In this first example, the path connecting the two non-body-part entities within one pair via one body part entity will be considered. We will use A-(B)-A to represent such path, wherein A represents the abnormality entity, B represents the body part entity, and, "( )" represents a "hub".

In the example as shown in FIGS. 2 and 3, four different abnormalities, i.e., (i) nodule, (ii) lymph node enlargement, (iii) cavity, and (iv) emphysematous variation, are extracted in the step S120. Thus, in the step S130, the relevance score are computed for each pair of all possible pairs of these four different abnormalities. All possible pairs of these four different abnormalities comprise the following pairs: (i) and (i), (i) and (ii), (i) and (iii), (i) and (iv), (ii) and (ii), (ii) and (iii), (ii) and (iv), (iii) and (iii), (iii) and (iv), and (iv) and (iv). In the table in the middle of FIG. 6, the computed relevance scores are shown. It can be understood that, in view of that the relevance score for the pair comprising two same abnormalities will be 1, such pair may not be considered in some cases.

Below, the computation of the relevance score for the pair of (i) nodule and (ii) lymph node enlargement will be described in details. It can be understood that the relevance score for another pair may be computed similarly.

First, a graph such as the one shown in FIG. 5 is built based on in a plurality of historical radiology reports of the patient x, and, a large amount of the graphs may be built similarly for respective patients. For example, the historical radiology reports of different patients made during the last month, the last six months, or the last year by the radiology department of a hospital may be used to build the large amount of the graphs.

Second, on the basis of the built graphs, the number of the paths connecting (i) nodule and (ii) lymph node enlargement the historical radiology reports may be counted. In particular, the number of the paths in the form of A-(B)-A will be counted. As shown in the upper table of FIG. 6, for example, if the nodule is found at the vocal cord film in one report of the patient X, and the lymph node enlargement is also found at the vocal cord film in another report of the patient X, then the path "nodule—vocal cord film—lymph node enlargement" can be built. Alternatively, the concerned reports may be from different patients. Similarly, the paths "nodule—thyroid—lymph node enlargement", "nodule—sinoatrial node—lymph node enlargement", "nodule—apex of lung—lymph node enlargement", and "nodule—abdominal cavity—lymph node enlargement" may also be built. The counts of the different paths are noted in the most right side column of the upper table in FIG. 6. The sum of these counts or count values may represent the number of the paths on which these two abnormalities (i) nodule and (ii) lymph node enlargement co-occur, and may be further used for computing the relevant score between the two abnormalities (i) nodule and (ii) lymph node enlargement.

Third, the relevance score between the two abnormalities (i) nodule and (ii) lymph node enlargement is computed using the count. The relevance score may be computed using the above equation (1). In this example, the count C1 is 25+64+37+74+28=228, the count C2, which is not shown, is 25, and thus the relevance score is about 0.9, which is noted in the table in the middle of FIG. 6. Similarly, the relevance scores between the two abnormalities in each of other pairs are computed and noted in the table in the middle of FIG. 6. The relevance scores of the all possible pairs then may be used for clustering the four abnormalities extracted from the input radiology report.

In this example, in view of that there are three disorders that appear in the impression part, the four abnormalities may be clustered into three clusters. As mentioned previously, the k-means algorithm may be used for the clustering. Alternatively, in this example, since the four abnormalities are to be clustered into three clusters, the highest relevant score 0.9, the lowest relevant score 0.1, and the second lowest relevant score 0.2 are used to group the four abnormalities into three groups, as shown in FIG. 6.

Then, the body part entity or entities related to the non-body-part entity or entities clustered in each of the clusters (or groups) are output as one diagnosis object. That is, the right lung S5, the right hilar, and the mediastinum, may be output as a first diagnosis object; the left middle lobe may be output as a second diagnosis object; and, the left upper lobe may be output as a third diagnosis object. In other words, the following diagnosis objects will be output, wherein the entities within { } are treated as one diagnosis object:

{right lung S5, right hilar, mediastinum};
{left middle lobe};
{left upper lobe}.

Further, optionally, these diagnosis objects may be further related to disorders that appear in the impression part of the report based on the known medical knowledge. For example, the following information may be output:

{right lung S5, right hilar, mediastinum}/primary lung cancer;
{left middle lobe}/honeycomb lung;
{left upper lobe}/pulmonary emphysema.

Thus, the diagnosis-dependent diagnosis objects may be extracted and output. The above output indicates that, the right lung S5, the right hilar, and the mediastinum are considered together to make the diagnosis with respect to "primary lung cancer". Similarly, the left middle lobe is considered to make the diagnosis with respect to "'honeycomb lung", and the left upper lobe is considered to make the diagnosis with respect to "pulmonary emphysema".

Further, with respect to the Report 2 given in the background portion, the output obtained with use of the method described in this first example will be:

{right lung S5}/lung cancer;
{right hilar, mediastinum,
left middle lobe}/interstitial pneumonia;
{left upper lobe}/discoid atelectasis.

The above output indicates that, the right lung S5 is considered to make the diagnosis with respect to "lung cancer". The right hilar, the mediastinum, and the left middle lobe are considered together to make the diagnosis with respect to "interstitial pneumonia", and the left upper lobe is considered to make the diagnosis with respect to "discoid atelectasis".

As can be seen, according to the method of the invention, the entities in a medical document can be partitioned into diagnosis-dependent groups. In other words, the entities in a medical document can be grouped according to the diagnoses made therein.

With use of such diagnosis-dependent groups, it may be easy to associate a diagnosis with an object region in an image, and it may be easy to analyze and compare radiology reports. And, this may be advantageous for facilitating the work of a radiologist, for example, for avoiding missing the exam on any body part necessary for making the diagnose.

Note that, the number of the clusters to be clustered is not limited to the number of the disorders that appear in the radiology report. The number of the clusters to be clustered may be determined to be other values as appropriate.

Second Example (Use of the Path A-(B)-A-(B)-A)

Next, the second example will be described with reference to FIG. 6. The second example is the same as the first example except that a path in a different form connecting the two non-body-part entities within one pair is considered. In particular, the path connecting the two non-body-part entities within one pair to a third non-body-part entity via two body part entities is considered, in more particular, the path connecting two abnormalities to a third abnormality via two body part entities is considered. We use A-(B)-A-(B)-A to represent such path, wherein A represents the abnormality entity, B represents the body part entity, and, "( )" represents a "hub". This path means that two abnormalities co-occur with the same abnormality.

As can be seen from FIG. 6, a path "nodule—sinoatrial node—hypertrophy—left atrium—lymph node enlargement" is built. This path means the abnormalities "nodule" and "lymph node enlargement" co-occur with a third abnormality "hypertrophy". The count or the counted value of such path is 5. This count may be separately used for computing the relevance score between the abnormalities (i) nodule and (ii) lymph node enlargement. In particular, both this count and the count of the path in the form of A-(B)-A-(B)-A on which merely one of the abnormalities "nodule" and "lymph node enlargement" occurs at either one of the two ends thereof may be used for performing the computation. Alternatively, this count may be used in combination with the count for the path A-(B)-A for computing the relevance score. That is, this count will be further added to the count for the path A-(B)-A in the first example to obtain the number of the count of the paths connecting the abnormalities (i) nodule and (ii) lymph node enlargement.

The following relevance score computation process, clustering process, and outputting process are the similar to those in the first example.

In the second example, the same advantages as those in the first example may be obtained. Further, with use of the path in the form of A-(B)-A-(B)-A, the diffusion of a disorder may be observed. In addition, such diffusion of a disorder may be prompted to a radiologist.

Third Example (Use of the Path A-(B)-D-(B)-A)

Next, the third example will be described with reference to FIG. 6. The third example is the same as the first example except that a path in a different form connecting the two non-body-part entities within one pair is considered. In particular, also the path connecting the two non-body-part entities within one pair to a third non-body-part entity via two body part entities is considered, but the path connecting two abnormalities to a disorder via two body part entities is considered. We use A-(B)-D-(B)-A to represent such path, wherein A represents the abnormality entity, B represents the body part entity, D represents the disorder, and, "( )" represents a "hub". This path means that two abnormalities co-occur with the same disorder.

As can be seen from FIG. 6, the path "nodule—apex of lung—lung cancer—pleura—lymph node enlargement" and "nodule—thyroid—thyroncus—thyroid—lymph node enlargement" are built. The former one means that the abnormalities "nodule" and "lymph node enlargement" are the abnormalities of the same disorder "lung cancer". Similarly, the latter one means that the abnormalities "nodule" and "lymph node enlargement" are the abnormalities of the same disorder "thyroncus". Note that in the latter path, the two body parts used as the connection points are the same body part "thyroid". That is to say, the two body parts used as the connection points may be the same or not. Although it is not exemplified in the second example, but this point is also true for the path in the form of A-(B)-A-(B)-A. The count or the counted value of such path is 56+12=68. Similarly, this count may be separately used for computing the relevance score between the abnormalities (i) nodule and (ii) lymph node enlargement. In particular, both this count and the count of the paths in the form of A-(B)-D-(B)-A on which merely one of the abnormalities "nodule" and "lymph node enlargement" occurs at either one of the two ends thereof may be used for performing the computation. Alternatively, this count may be used in combination with at least one of the count for the path A-(B)-A and the count for the path A-(B)-A-(B)-A for computing the relevance score. That is, this count will be further added to at least one of the count for the path A-(B)-A and the count for the path A-(B)-A-(B)-A to obtain the count of the number of the paths connecting the abnormalities (i) nodule and (ii) lymph node enlargement.

The following computation of the relevance score process, clustering process, and outputting process are the similar to those in the first example.

The following relevance score computation process, clustering process, and outputting process are the similar to those in the first example.

In the third example, the same advantages as those in the first example may be obtained. Further, with use of the path in the form of A-(B)-D-(B)-A, the diffusion of a disorder may be observed. In addition, such diffusion of a disorder may be prompted to a radiologist.

Note that, although in the above three examples, two abnormalities are used as the two non-body-part entities within one pair, it can be understood that other types of the non-body-part entities may be used to replace one or both of the abnormality entities. For example, a path in the form of A-(B)-S, S-(B)-S, A-(B)-R, E-(B)-R, A-(B)-S-(B)-A, A-(B)-D-(B)-S, or the like may be considered, wherein S represents the signal, R represents the request, and E represents the exam.

Note that, although in the above three examples, the length of the path is limited, it can be understood that the longer path, such as A-(B)-A-(B)-A-(B)-A or A-(B)-D-(B)-A-(B)-D-(B)-A, may also be considered. But it should note that, with the increase of the length of the path, the reliability of the computed relevant score might be lowered.

Note that, referring to FIG. 3, if the abnormality "cavity" also relates to the body part "right lung S5", then this abnormality "cavity" related to "right lung S5" will be treated as a abnormality different from the abnormality "cavity" related to "left middle lobe". And, the relevance score between them will be computed with both of them deemed as two kinds of different abnormalities.

Optionally, the step S130 may further comprise assigning a weight to each of the paths using a pre-defined rule, and computing the relevance score using the count and the weight of each of the paths. In particular, in one embodiment of the present disclosure, before the step S403 of computing the relevance scores, there may be an optional step of assigning a weight to each of the paths using a pre-defined rule.

For example, if the paths A-(B)-A, A-(B)-A-(B)-A, and A-(B)-D-(B)-A all are considered when the number of the paths is counted, then these three kinds of paths may be assigned different weights. For example, if the diffusion of a disorder is deemed as being more important (corresponding to the pre-defined rule), then the weights assigned to the latter two kinds of the paths may be greater than the weight assigned to the first kind of the path. Assuming that the weight W2 is given to the each of the paths A-(B)-A-(B)-A and A-(B)-D-(B)-A, while the weight W1 is given to the path A-(B)-A, wherein W2>W1, then the relevance score between, for example, two abnormalities within one pair may be computed according to the following equation (2):

[Math.2]
$$S = \frac{C11 \cdot W1 + C12 \cdot W2}{(C11 + C21) \cdot W1 + (C12 + C22) \cdot W2} \quad (2)$$

wherein S represents the relevance score between the two abnormalities within one pair, C11 represents the count of the number of the paths in the form of A-(B)-A on which the two abnormalities within one pair co-occur, C21 represents the count of the number of the paths in the form of A-(B)-A on which the two abnormalities within one pair do not co-occur, C12 represents the count of the number of the paths in the forms of A-(B)-A-(B)-A and A-(B)-D-(B)-A on which the two abnormalities within one, pair co-occur, C22 represents the count of the number of the paths in the forms of A-(B)-A-(B)-A and A-(B)-D-(B)-A on which the two abnormalities within one pair do not co-occur. The relevance score S may take a value greater than or equal to 0 and smaller than or equal to 1. The count C11, C21, C12, or C22 may take a positive integer value greater than or equal to 0. The weight W1 or W2 may take a value greater than or equal to 0 and smaller than or equal to 1.

Note that, the above predetermined rule are merely illustrative, and other pre-defined rules may be employed as appropriate. Further, the above equation (2) is merely illustrative, too, and the present invention is not limited thereto.

Next, the process of labelling an image related to the input radiology report using one or more diagnosis objects will be described in details with reference to FIG. 7. At the left side of FIG. 7, an input radiology report, which is the same report as the one of FIG. 2, and its related radiological image are shown. After being processed according to the method of the invention as described above, the output may be the table shown at the right side of FIG. 7.

As shown in the lower right corner of FIG. 7, the related radiological image is labelled according to the three diagnosis objects. That is, the body parts within the first diagnosis object are labelled with the number "1", the body parts within the second diagnosis object are labelled with the number "2", and the body parts with the third diagnosis object are labelled with the number "3". Such labelling may facilitate the work of a radiologist. For example, such labelling may be advantageous for avoiding missing the exam on any body part necessary for making the diagnose.

Next, FIG. 8 is a block diagram showing an apparatus 800 for extracting a diagnosis object from an input medical document according to the present embodiment of the present disclosure. The blocks of the apparatus 800 may be implemented by hardware, software, firmware, or any combination thereof to carry out the principles of the present disclosure. It is understood by those skilled in the art that the blocks described in FIG. 8 may be combined or separated into sub-blocks to implement the principles of the present disclosure as described above. Therefore, the description herein may support any possible combination or separation or further definition of the blocks described herein.

As shown in FIG. 8, the apparatus 800 comprises an entity and relation extraction section 810, a relevance score obtaining section 820, a clustering section 830, and a diagnosis object outputting section 840. Optionally, apparatus 800 further comprises an image labelling section 850. The entity and relation extraction section 810 may be configured to extract, from an input medical document, body part entities and at least one type of non-body-part entities and the relations between the body part entities and the non-body-part entities. The relevance score obtaining section 820 may be configured to obtain, for each pair of all possible pairs of the non-body-part entities, a relevance score between two non-body-part entities within one pair, wherein the relevance score is obtained by using the relations between the two non-body-part entities within one pair and one or more body part entities in a plurality of historical medical documents. The clustering section 830 may be configured to cluster the non-body-part entities in the input medical document into one or more clusters based on the relevance scores of the all possible pairs. The diagnosis object outputting section 840 may be configured to output one or more body part entities related to one or more non-body-part entities clustered in each of the clusters as one diagnosis object. The image labelling section 850 may be configured to label an image related to the input medical document using one or more diagnosis objects.

Although it is not shown in FIG. 8, FIG. 8 may further comprises a reception section configured to receive an input medical document.

The relevance score obtaining section 820 may further comprises a graph building section 821, a path number counting section 822, and a relevance score computation section 823. The relevance score obtaining section 820 may further optionally comprises a weight assignment section 824. The graph building section 821 may be configured to build a graph by connecting one non-body-part entity to another if both of them are related to the same body part entity and repeating such connection across a plurality of the historical medical documents based on the data from the plurality of historical medical documents. The path number counting section 822 may be configured to count, for each pair of the all possible pairs of the non-body-part entities, a number of paths connecting two non-body-part entities within one pair in the historical medical documents. And, the relevance score computation section 823 may be configured to compute, for each pair of the all possible pairs of the non-body-part entities, the relevance score between the two non-body-part entities within one pair using the count. For example, for each pair of the all possible pairs of the non-body-part entities, the relevance score may be computed according to the above mentioned equation (1). The weight assignment section 824 may be configured to assign a weight to each of the paths using a pre-defined rule. If the weight assignment section 824 exists, then the relevance score computation section 823 may compute the relevance score using the count and the weight of each of the paths, for example, according to the above equation (2). Note that, the graph building section 821 and the path number counting section 822 correspond to the path building and counting section.

Alternatively, if the relevance scores of various pairs of two non-body-part entities are pre-computed and pre-stored, the relevance score obtaining section 820 may be configured to retrieve the pre-stored relevance scores as needed.

Second Embodiment

Next, the second embodiment of the invention will be described. The second embodiment is the same as the first embodiment except that, one or more non-body-part entities clustered in one cluster, instead of one or more body part entities related thereto, are output as one diagnosis object.

Still taking the input radiology report of FIG. 2 as an example, in the first embodiment, the right lung S5, the right hilar, and the mediastinum, may be output as a first diagnosis object; the left middle lobe may be output as a second diagnosis object; and, the left upper lobe may be output as a third diagnosis object. In this second embodiment, instead of outputting three clusters of the body part entities, three clusters of the non-body-part entities may be output as three diagnosis objects, respectively. In particular, the following diagnosis objects may be output:
{nodule, lymph node enlargement};
{cavity};
{emphysematous variation}.

It can be understood that the second embodiment may be combined with the first embodiment. For example, one or more non-body-part entities within one cluster may be separately output as one diagnosis object or may be output together with one or more related body part entities as one diagnosis object. For another example, these non-body-part entities may be further related to the disorders that appear in the impression part of the input radiology report. Various aspects of the first embodiment may be combined with the second embodiment, unless it is explicitly stated that the combination is not allowed or the combination is not logical.

The apparatus 800' for achieving the second embodiment may comprise the entity and relation extraction section 810, the relevance score obtaining section 820, and the clustering section 830 as shown in FIG. 8 and a diagnosis object outputting section 840'. This diagnosis object outputting section 840' may be configured to output, as one diagnosis object, one or more non-body-part entities clustered in each of the clusters and/or one or more body part entities related thereto. The apparatus 800' may optionally comprise the image labelling section 850 as shown in FIG. 8.

Third Embodiment

Next, the third embodiment of the invention will be described. The third embodiment is applicable to segment text in an input medical document. In this third embodiment, based on the diagnosis objects determined in the above first or second embodiments, the text in an input medical document is segmented such that one or more non-body-part entities clustered in each of the clusters and one or more body part entities related thereto occur in one segment.

Still taking the input radiology report of FIG. 2 as an example, after the text segmenting process according to the third embodiment, the following segmented text may be output, wherein the " . . . " represents different segments:

Image Observations

{A nodule of about 3 cm in the right lung S5 is observed. The right hilar and mediastinum lymph node enlargement is observed.}
{It is observed that a diffuse cavity is formed in the left middle lobe.}
{An emphysematous variation in the left upper lobe is observed. A bulla with a major diameter of 7 cm is seen.}

Although in this example, the text in the input medical document is segmented sequentially, it can be understood that, the text is segmented according to the extracted diagnosis objects. That is, the text related to one diagnosis object will be segmented into one segment. Thus, if it is assumed that both the right lung S5 and the left middle lobe are grouped into one cluster, then the order of the third sentence related to the left middle lobe will be adjusted to be after the first sentence, such that the first sentence related to the right lung S5 and the third sentence related to the left middle lobe can be segmented into one segment.

The apparatus 800" for achieving the third embodiment may comprise the entity and relation extraction section 810, the relevance score obtaining section 820, and the clustering section 830 as shown in FIG. 8 and a text segmenting section 860 configured to segment the text in the input medical document such that one or more non-body-part entities clustered in each of the clusters and one or more body part entities related thereto occur in one segment.

It can be understood that the third embodiment may be combined with the first embodiment and/or the second embodiment. Various aspects of the first and second embodiments may be combined with the third embodiment, unless it is explicitly stated that the combination is not allowed or the combination is not logical.

Hardware Implementation

FIG. 9 illustrates a general hardware environment 900 wherein at least one of the above first to third embodiments is applicable in accordance with an exemplary embodiment of the present disclosure.

With reference to FIG. 9, a computing device 900, which is an example of the hardware device that may be applied to the aspects of the present disclosure, will now be described. The computing device 900 may be any machine configured to perform processing and/or calculations, may be but is not limited to a work station, a server, a desktop computer, a laptop computer, a tablet computer, a personal data assistant, a smart phone, an on-vehicle computer or any combination thereof. The aforementioned apparatus 800/800'/800" may be wholly or at least partially implemented by the computing device 900 or a similar device or system.

The computing device 900 may comprise elements that are connected with or in communication with a bus 902, possibly via one or more interfaces. For example, the computing device 900 may comprise the bus 902, and one or more processors 904, one or more input devices 906 and one or more output devices 908. The one or more processors 904 may be any kinds of processors, and may comprise but are not limited to one or more general-purpose processors and/or one or more special-purpose processors (such as special processing chips). The input devices 906 may be any kinds of devices that can input information to the computing device, and may comprise but are not limited to a mouse, a keyboard, a touch screen, a microphone and/or a remote control. The output devices 908 may be any kinds of devices that can present information, and may comprise but are not limited to display, a speaker, a video/audio output terminal, a vibrator and/or a printer. The computing device 900 may also comprise or be connected with non-transitory storage devices 910 which may be any storage devices that are non-transitory and can implement data stores, and may comprise but are not limited to a disk drive, an optical storage device, a solid-state storage, a floppy disk, a flexible disk, hard disk, a magnetic tape or any other magnetic medium, a compact disc or any other optical medium, a ROM (Read Only Memory), a RAM (Random Access Memory), a cache memory and/or any other memory chip or cartridge, and/or any other medium from which a computer may read data, instructions and/or code. The non-transitory storage devices 910 may be detachable from an interface. The non-transitory storage devices 910 may have data/instructions/code for implementing the methods and steps which are described above. The computing device 900 may also comprise a communication device 912. The communication device 912 may be any kinds of device or system that can enable communication with external apparatuses and/or with a network, and may comprise but are not limited to a modem, a network card, an infrared communication device, a wireless communication device and/or a chipset such as a Bluetooth™ device, 1302.11 device, WiFi device, WiMax device, cellular communication facilities and/or the like.

The bus 902 may include but is not limited to Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

The computing device 900 may also comprise a working memory 914, which may be any kind of working memory that may store instructions and/or data useful for the working of the processor 904, and may comprise but is not limited to a random access memory and/or a read-only memory device.

Software elements may be located in the working memory 914, including but are not limited to an operating system 916, one or more application programs 918, drivers and/or other data and codes. Instructions for performing the methods and steps described in the above may be comprised in the one or more application programs 918, and the sections of the aforementioned apparatus 800/800'/800" may be implemented by the processor 904 reading and executing the instructions of the one or more application programs 918. More specifically, entity and relation extraction section 810 of the aforementioned apparatus 800/800'/800" may, for example, be implemented by the processor 904 when executing an application 918 having instructions to perform the step S120. In addition, the relevance score obtaining section 820 of the aforementioned apparatus 800/800'/800" may, for example, be implemented by the processor 904 when executing an application 918 having instructions to perform the step S130 or the steps S401-403. Other sections of the aforementioned apparatus 800/800'/800" may also, for example, be implemented by the processor 904 when executing an application 918 having instructions to perform one or more of the aforementioned respective steps. The executable codes or source codes of the instructions of the software elements may be stored in a non-transitory computer-readable storage medium, such as the storage device(s) 910 described above, and may be read into the working memory 914 possibly with compilation and/or installation. The executable codes or source codes of the instructions of the software elements may also be downloaded from a remote location.

Note that, the present disclosure also provides a non-transitory computer readable medium having instructions stored thereon that, when executed by a processor, causing the processor to perform the steps of each of the above mentioned methods of the first to third embodiments.

It is possible to carry out the method and apparatus of the present disclosure in many ways. For example, it is possible to carry out the method and apparatus of the present disclosure through software, hardware, firmware or any combination thereof. The above described order of the steps for the method is only intended to be illustrative, and the steps of the method of the present disclosure are not limited to the above specifically described order unless otherwise specifically stated. Besides, in some embodiments, the present disclosure may also be embodied as programs recorded in recording medium, including machine-readable instructions for implementing the method according to the present disclosure. Thus, the present disclosure also covers the recording medium which stores the program for implementing the method according to the present disclosure.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Chinese Patent Application No. 201610177996.2, filed Mar. 25, 2016, which is hereby incorporated by reference herein in its entirety.

The invention claimed is:

1. A method for extracting a diagnosis object from a medical document, characterized in comprising:
   extracting, from a plurality of medical documents, one or more body part entities, one or more non-body-part entities and relations between the one or more body part entities and the one or more non-body-part entities;
   obtaining a relevance score between two non-body-part entities within one pair, wherein the relevance score is obtained by using the relations between the one or more body part entities and the one or more non-body-part entities based on whether or not the two non-body-part entities are related to the same body part entity in the plurality of medical documents;

clustering the one or more non-body-part entities in the medical document into one or more clusters based on the relevance score; and outputting the one or more body part entities related to the one or more non-body-part entities clustered in the one or more clusters as the diagnosis object.

2. The method of claim 1, wherein the at least one type of non-body-part entities comprises at least one of abnormality, disorder, signal, request, exam, treatment, and drug.

3. The method of claim 1, wherein extracting the relations between the body part entities and the non-body-part entities further comprises:

extracting a relation between a body part entity and a non-body-part entity using a relation extraction algorithm; or extracting a relation between a body part entity and a non-body-part entity if the body part entity and the non-body-part entity co-occur within a context.

4. The method of claim 1, wherein extracting the relations between the body part entities and the non-body-part entities further comprises:

if a non-body-part entity has no explicit relation with any body part entity, assigning a default related body part entity to it using a knowledge-base or zero anaphora resolution algorithm.

5. The method of claim 1, wherein obtaining the relevance score further comprises:

counting a number of paths connecting the two non-body-part entities within one pair in the historical medical documents, wherein the paths are built by connecting one non-body-part entity to another non-body-part entity if both of them are related to the same body part entity; and computing the relevance score using the count.

6. The method of claim 5, wherein the paths connecting the two non-body-part entities within one pair comprise at least one of:

(i) a path connecting the two non-body-part entities within one pair via one body part entity; and (ii) (ii) a path connecting the two non-body-part entities within one pair to a third non-body-part entity via two body part entities.

7. The method of claim 5, wherein counting the number of paths further comprises:

filtering the paths using a property of non-body-part entity as a constraint, wherein the property of non-body-part entity comprise at least one of polarity, patient ID, patient age, patient sex, time span between exams, and body part ontology.

8. The method of claim 5, wherein obtaining the relevance score further comprises:

assigning a weight to each of the paths using a pre-defined rule; and computing the relevance score using the count and the weight of each of the paths.

9. The method of claim 1, wherein the relevance scores of the all possible pairs are pre-computed offline and pre-stored, and wherein obtaining the relevance score further comprises retrieving the pre-stored relevance score.

10. The method of claim 1, further comprising: labelling an image related to the input medical document using one or more diagnosis objects.

11. An apparatus for extracting a diagnosis object from a plurality of medical documents, characterized in comprising:

a memory configured to store a series of computer executable instructions; and at least a processor configured to execute said series of computer executable instructions, wherein said series of computer executable instructions, when executed by the at least processor, cause the at least processor to perform the method of claim 1.

12. A method for extracting a diagnosis object from a plurality of medical documents, characterized in comprising:

extracting, from the plurality of medical documents, one or more body part entities, one or more non-body-part entities, and relations between the one or more body part entities and the one or more non-body-part entities;

obtaining a relevance score between two non-body-part entities within one pair, wherein the relevance score is obtained by using the relations between the one or more body part entities and the one or more non-body-part entities based on whether or not the relations between the two non-body-part entities are related to the same body part entity in the plurality of medical documents;

clustering the one or more non-body-part entities in the plurality of medical documents into one or more clusters based on the relevance score; and outputting the one or more non-body-part entities clustered in the one or more clusters as the diagnosis object.

13. A method for segmenting text in a plurality of medical documents, characterized in comprising:

extracting, from the plurality of medical documents, one or more body part entities, one or more non-body-part entities, and relations between the one or more body part entities and the one or more non-body-part entities;

obtaining a relevance score between two non-body-part entities within one pair, wherein the relevance score is obtained by using relations between the one or more body part entities and the one or more non-body entities based on whether or not the two non-body-part entities are related to the same body part entity in the plurality of medical documents;

clustering the one or more non-body-part entities in the plurality of medical documents into one or more clusters based on the relevance score; and segmenting the text in the medical document such that one or more non-body-part entities clustered in the one or more clusters and the one or more body part entities related thereto occur in one segment.

14. An apparatus for segmenting text in a plurality of medical documents, characterized in comprising:

a memory configured to store a series of computer executable instructions; and at least a processor configured to execute said series of computer executable instructions, wherein said series of computer executable instructions, when executed by the at least processor, cause the at least processor to perform the method of claim 13.

15. An apparatus for extracting a diagnosis object from a plurality of medical documents, characterized in comprising:

a memory storing a program; and one or more processors which, by executing the program, function as:

an entity extraction section configured to extract, from the plurality of medical documents, one or more body part entities, one or more non-body-part entities, and relations between the one or more body part entities and the one or more non-body part entities;

a relevance score obtaining section configured to obtain a relevance score between two non-body-part entities within one pair, wherein the relevance score is obtained by using the relations between the one or more body part entities and the one or more non-body part entities based on whether or not the two non-body-part entities are related to the same body part entity in the plurality of medical documents;

a clustering section configured to cluster the one or more non-body-part entities in the plurality of medical documents into one or more clusters based on the relevance score; and a diagnosis object outputting section configured to output the one or more body part entities related to one or more non-body-part entities clustered in the one or more clusters as the diagnosis object.

16. The apparatus of claim 15, wherein the at least one type of non-body-part entities comprises at least one of abnormality, disorder, signal, request, exam, treatment, and drug.

17. The apparatus of claim 15, wherein the entity and relation extraction section is further configured to:

extract a relation between a body part entity and a non-body-part entity using a relation extraction algorithm; or extracting a relation between a body part entity and a non-body-part entity if the body part entity and the non-body-part entity co-occur within a context.

18. The apparatus of claim 15, wherein the entity and relation extraction section is further configured to:

if a non-body-part entity has no explicit relation with any body part entity, assigning a default related body part entity to it using a knowledge-base or zero anaphora resolution algorithm.

19. The apparatus of claim 15, wherein the relevance score obtaining section further comprises:

a path building and counting section configured to count a number of paths connecting the two non-body-part entities within one pair in the historical medical documents, wherein the paths are built by connecting one non-body-part entity to another non-body-part entity if both of them are related to the same body part entity; and a relevance score computation section configured to compute the relevance score using the count.

20. The apparatus of claim 19, wherein the paths connecting the two non-body-part entities within one pair comprise at least one of:

(i) a path connecting the two non-body-part entities within one pair via one body part entity; and (ii) (ii) a path connecting the two non-body-part entities within one pair to a third non-body-part entity via two body-part entities.

21. The apparatus of claim 19, wherein the path building and counting section is further configured to:

filter the paths using a property of non-body-part entity as a constraint, wherein the property of non-body-part entity comprise at least one of polarity, patient ID, patient age, patient sex, time span between exams, and body part ontology.

22. The apparatus of claim 19, wherein the relevance score obtaining section further comprises:

a weight assignment section configured to assign a weight to each of the paths using a pre-defined rule; and wherein the relevance score computation section is further configured to compute the relevance score using the count and the weight of each of the paths.

23. The apparatus of claim 15, wherein the relevance scores of the all possible pairs are pre-computed offline and pre-stored, and wherein obtaining the relevance score further comprises retrieving the pre-stored relevance score.

24. The apparatus of claim 15, further comprising:

an image labelling section configured to label an image related to the input medical document using one or more diagnosis objects.

25. An apparatus for extracting a diagnosis object from a plurality of medical documents, characterized in comprising:

a memory storing a program; and one or more processors which, by executing the program, function as:

an entity extraction section configured to extract, the plurality of medical documents, one or more body part entities, one or more non-body-part entities, and relations between the one or more body part entities and the non-body-part entities;

a relevance score obtaining section configured to obtain a relevance score between two non-body-part entities within one pair using the relations between the one or more body part entities and the non-body-part entities based on whether or not the two non-body-part entities are related to the same body part entity in the plurality of medical documents;

a clustering section configured to cluster the one or more non-body-part entities in the plurality of medical documents into one or more clusters based on the relevance score; and a diagnosis object outputting section configured to output the one or more non-body-part entities clustered in the one or more clusters as the diagnosis object.

26. An apparatus for segmenting text in a plurality of medical documents, characterized in comprising:

a memory storing a program; and one or more processors which, by executing the program, function as:

an entity extraction section configured to, from the plurality of medical documents, one or more body part entities, one or more non-body-part entities, and relations between the one or more body part entities and the one or more non-body part entities;

a relevance score obtaining section configured to obtain a relevance score between two non-body-part entities within one pair, wherein the relevance score is obtained by using the relations between the body-part entities and the non-body-part entities based on whether or not the two non-body-part entities are related to the same body part entity in the plurality of medical documents;

a clustering section configured to cluster the one or more non-body-part entities in the plurality of medical documents into one or more clusters based on the relevance score; and a text segmenting section configured to segment the text in the medical document such that one or more non-body-part entities clustered in the or more clusters and the one or more body part entities related thereto occur in one segment.

* * * * *